Figure 1:
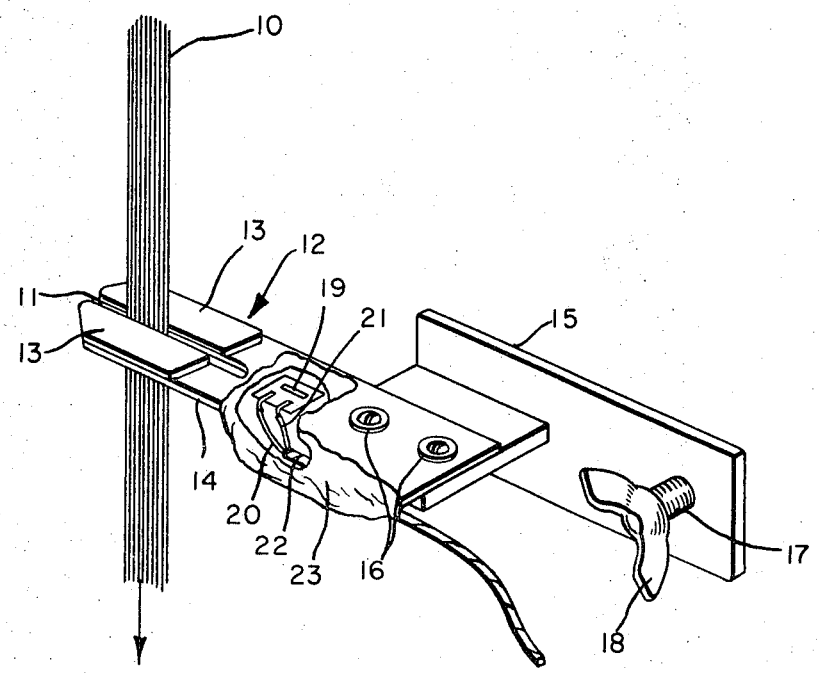
Figure 2:
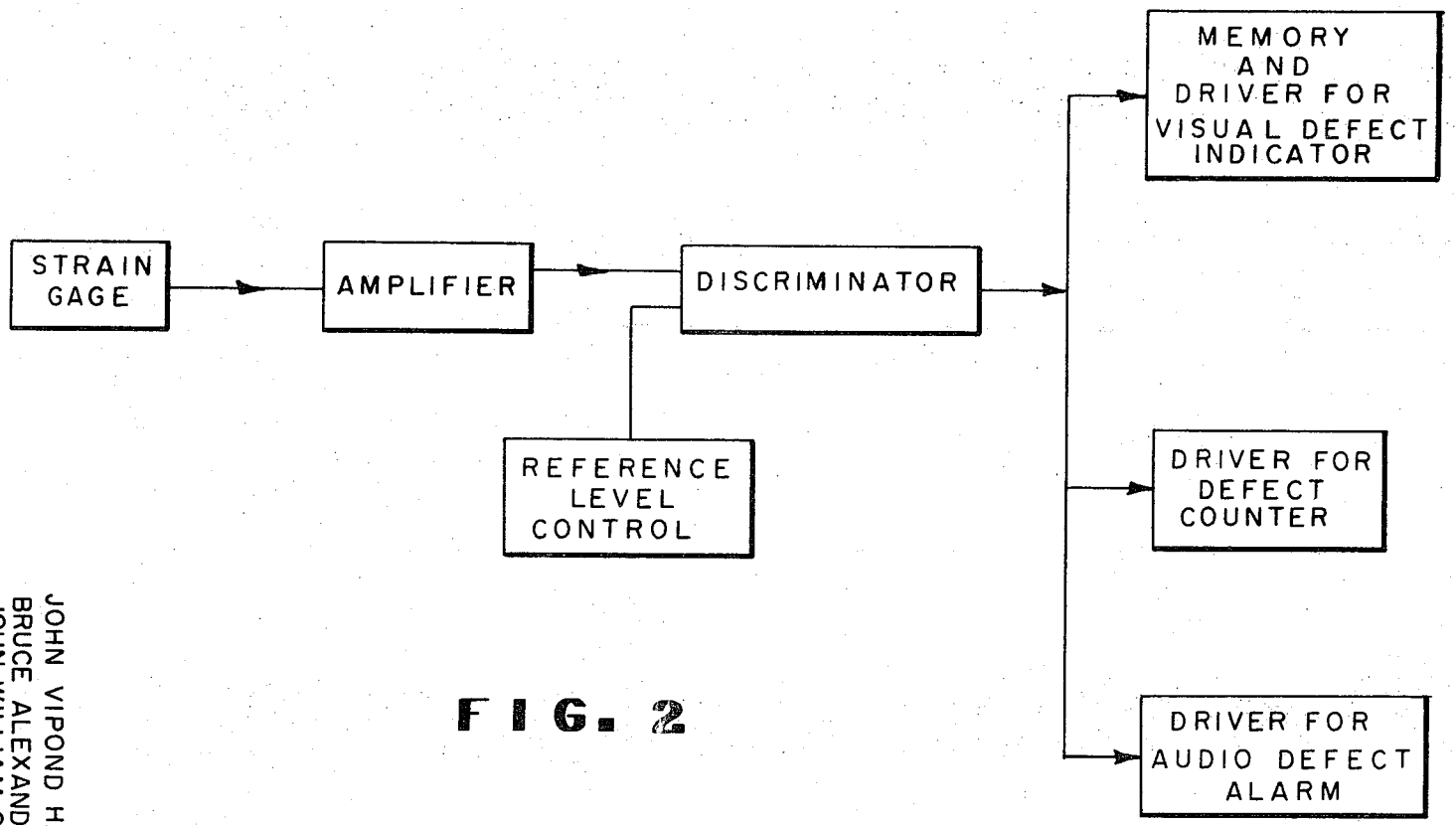

DEFENSIVE PUBLICATION

UNITED STATES PATENT OFFICE

Published at the request of the applicant or owner in accordance with the Notice of Dec. 16, 1969, 869 O.G. 687. The abstracts of Defensive Publication applications are identified by distinctly numbered series and are arranged chronologically. The heading of each abstract indicates the number of pages of specification, including claims and sheets of drawings contained in the application as originally filed. The files of these applications are available to the public for inspection and reproduction may be purchased for 30 cents a sheet.

Defensive Publication applications have not been examined as to the merits of alleged invention. The Patent Office makes no assertion as to the novelty of the disclosed subject matter.

PUBLISHED MAY 4, 1971

886 O.G. 5

T886,007

APPARATUS FOR DETECTING OVERSIZE DEFECTS IN YARN

John Vipond Harvey, 36 Campbell Crescent; Bruce Alexander Robinson, 3 Holland Crescent; and John William Stassen, 155 Division St., all of Kingston, Ontario, Canada

Filed May 4, 1970, Ser. No. 34,167

Int. Cl. G01n *19/08*

U.S. Cl. 73—160

2 Sheets Drawing. 6 Pages Specification

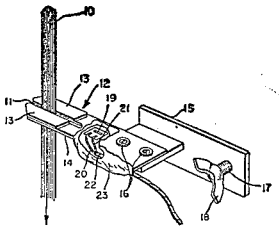

A device for detecting oversize defects in yarns or filaments comprising a slotted flexible guide 12 having a strain gauge 19 mounted thereon. The yarns or filaments 10 are passed through the slot 11 and a defect in the yarns or filaments causes the guide to deflect a distance according to the size of the defect. The deflection produces a signal from the strain gauge which is fed to a discriminator that compares the magnitude of the signal with a preset level and eliminates signals from small defects. The device is particularly adaptable in solvent spinning of synthetic fibers for detecting oversize filaments, and polymer drips.

May 4, 1971 J. V. HARVEY ETAL T886,007

APPARATUS FOR DETECTING OVERSIZE DEFECTS IN YARN

Filed May 4, 1970 2 Sheets-Sheet 1

INVENTORS
JOHN VIPON HARVEY
BRUCE ALEXANDER ROBINSON
JOHN WILLIAM STASSEN
BY Howard P. West Jr.
ATTORNEY

APPARATUS FOR DETECTING OVERSIZE DEFECTS IN YARN

Filed May 4, 1970 2 Sheets-Sheet 2

INVENTORS
JOHN VIPOND HARVEY
BRUCE ALEXANDER ROBINSON
JOHN WILLIAM STASSEN
BY Howard P. West Jr
ATTORNEY